US00PP24142P2

(12) United States Plant Patent
Conner

(10) Patent No.: US PP24,142 P2
(45) Date of Patent: Jan. 7, 2014

(54) MUSCADINE GRAPE PLANT NAMED 'GA. 5-1-45'

(50) Latin Name: *Vitis rotundifolia*
Varietal Denomination: Ga. 5-1-45

(75) Inventor: Patrick J. Conner, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 60 days.

(21) Appl. No.: 13/506,964

(22) Filed: May 29, 2012

(51) Int. Cl.
*A01H 5/00* (2006.01)

(52) U.S. Cl.
USPC ..... Plt./206

(58) Field of Classification Search
USPC ..... Plt./206, 205
See application file for complete search history.

*Primary Examiner* — Annette Para
(74) *Attorney, Agent, or Firm* — Klarquist Sparkman, LLP

(57) ABSTRACT

A new and distinct cultivar of the muscadine grape plant, *Vitis rotundifolia* Michx., named 'Ga. 5-1-45', which has: early ripening berries, typically beginning in the first week in August in Georgia; black berries; self-fertile flowers; berries with flesh that adheres to the skin (non-slip skin); berries that are firm in texture and with a high soluble solids content; and berries that are large for a self-fertile cultivar.

2 Drawing Sheets

BRIEF SUMMARY

The present invention comprises a new and distinct plant cultivar of *Vitis rotundifolia* Michx., which has been given the name 'Ga. 5-1-45'. My new variety has been asexually propagated in Tifton, Ga. by rooting cuttings under mist in the summer. The following unique combination of traits have been observed in the original plant of my variety and in asexually propagated progeny, when grown in Georgia, are firmly fixed, and which in combination distinguish it from existing cultivars:

1) Early ripening berries, typically beginning in the first week in August in Georgia.
2) Purple berries.
3) Self-fertile flowers.
4) Berries with flesh that adheres to the skin (non-slip skin), that are firm in texture and that have a high soluble solids content.
5) Berries which are large for a self-fertile cultivar.

Figure 1:
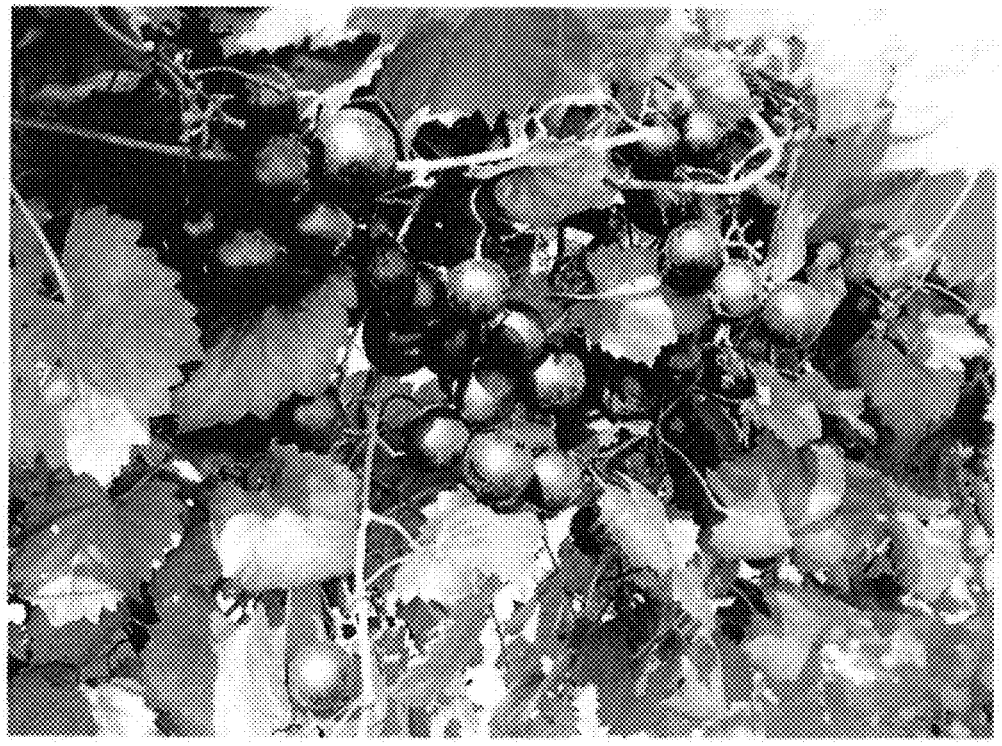
FIG. 1 is a detailed view of several clusters of ripe berries, obtained by clipping away some foliage.

Both Figures show the colors of the new variety as close to true color as is reasonably possible to obtain in colored reproductions of this type. Actual leaf and fruit colors may differ from leaf and fruit colors in the photograph due to light and environmental factors.

DETAILED DESCRIPTION

In the following description, color references are made to The Royal Horticultural Society Colour Chart, copyright 1966, except where general terms of ordinary dictionary significance are used.

BACKGROUND

The muscadine grape, *Vitis rotundifolia* Michx., is a popular fresh fruit grown in the Southeastern United States. In the Georgia climate, many cultivars ripen in early autumn when few other fruits are in season. The berries are large, as compared to other grape species, and are typically borne in clusters of 5-7 berries. Like many fruit crops, muscadine grapes are a heterozygous species and superior genotypes are clonally propagated. Nurseries typically propagate this species either by rooting softwood cuttings under mist, or by layering vines in the field.

The muscadine season in South Georgia begins in the last week of July and first week of August. At this time, growers begin picking the earliest ripening berries on the earliest cultivars. Unlike *vinifera* grapes, fresh-market muscadines are typically harvested as single berries by hand. Muscadines can vary in color from greenish-yellow (bronze) to pink, red, and purple, but stores often segregate them out as either bronze or purple/black. As consumers are often partial to one or the other color, a grower typically would like to have both colors available.

Numerous muscadine cultivars are of commercial importance. One muscadine production guide for Georgia lists 34 fresh market cultivars (nine are categorized as most recommended) and six processed grape cultivars. Even with this large number of cultivars, many are lacking desirable characteristics and growers are very interested in new cultivars with a higher combination of desirable traits. Currently, many commercial vineyards contain primarily female muscadine grape plants with a lesser number of self-fertile cultivars as the pollinator. Female cultivars have a yield that is often only about one-half that of self-fertile cultivars due to lack of pollination (flowers of female cultivars often don't open completely, blocking pollination). Despite the reduced productivity of most female cultivars, growers have continued to grow them because berry size and quality has typically been much larger in female cultivars than in self-fertile cultivars. Generally, growers want a berry size of at least 1 inch (2.5 cm) in diameter in a fresh-market cultivar. Provided minimum size and quality standards are met, more consistently productive self-fertile cultivars would be highly desirable.

Growers are also interested in early season cultivars, especially with purple berry color. Therefore, a need exists for an improved muscadine grape cultivar.

DETAILED DESCRIPTION

An initial cross 5-1 ('Supreme'×'Tara') was made by the inventor at the University of Ga., Tifton Campus as a part of a grape breeding program. 'Supreme' is the subject of U.S. Plant Pat. No. 7,267 and 'Tara' is unpatented. Fifty-five seedlings from this cross were germinated in a greenhouse and planted on the Tifton Campus in the spring of 2006. The original seedling vine of 'Ga. 5-1-45' was selected from this group of seedlings. This original 'Ga. 5-1-45' seedling first fruited in 2007 and was selected for propagation due to its very early harvest date, excellent flavor, and the characteristic of the flesh adhering to the skin. Cuttings were rooted at Tifton, Ga., and replicated trials were planted in the spring of 2008 at three locations in Tifton, Ga. Additional trials were planted in 2009 in Athens, Ga., Cullman, Ala., and in Ocilla, Ga.

Figure 2:
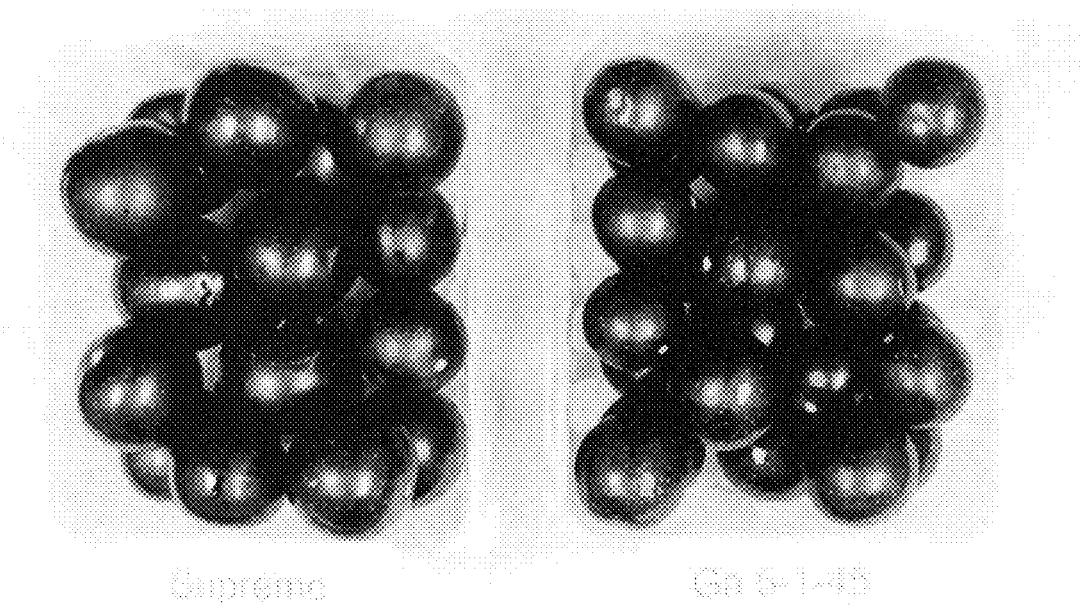
FIG. 2 is a view of ripe 'Ga. 5-1-45' berries (right) in a pint clamshell package in comparison to 'Supreme' (left).

'Ga. 5-1-45' fills a need as an early season, self-fertile, black berried grape plant (FIG. 2). Currently, the female cultivar 'Supreme' is the main purple fresh-market cultivar. 'Ga. 5-1-45' is superior to 'Supreme' because 'Ga. 5-1-45' has self-fertile flowers and ripens in the early harvest season (see Table 1 below), whereas 'Supreme' ripens mid-season. Ripening of 'Ga. 5-1-45' takes place in a relatively narrow window beginning the first week of August in Tifton, Ga. This is about 1 week before the standard early cultivar 'Tara' (unpatented) and the cultivar 'Nesbitt' (unpatented). The harvest of 'Ga. 5-1-45' is concentrated with picking occurring within a two-week window (see Table 1 below). Picking time of muscadine is primarily determined by soluble solids (sugar content) of the berries. 'Ga. 5-1-45' has consistently displayed very high soluble solids early in the season (see Table 4 below) indicating its potential as an early market cultivar. Berry size is large for a self-fertile cultivar at about 11 g and 25 mm in diameter growing in Tifton, Ga. (see Table 1, 2 below). Berries have a less pronounced muscadine aroma and flavor, similar to 'Supreme'. Berries are notable in that the flesh adheres to the skin (non-slip skin) and the flesh is firm in texture (see Table 3 below).

While 'Ga. 5-1-45' has a smaller berry weight than 'Supreme', 'Ga. 5-1-45' is comparable in size to the standard self-fertile cultivars 'Tara' (unpatented) and 'Nesbitt' (unpatented), and has a berry diameter of about an inch (2.6 cm) (see Table 2 below), making it acceptable to the industry. Additionally, 'Ga. 5-1-45' has a more consistent berry size than 'Supreme' (see Table 5 below). 'Supreme' tends to produce a mixture of extremely large and medium sized berries due to variation in seed number from partial pollination. Berry quality of 'Ga. 5-1-45' is high, the pulp is solid, and the skin adheres to the berry flesh. In these ways, the berry of 'Ga. 5-1-45' is similar to 'Supreme'. Due to the firm flesh of 'Ga. 5-1-45' berries, berry firmness remains high after cold storage (see Table 3 below). Year three (mature vine) yield of 'Ga. 5-1-45' was not significantly different from 'Tara' or 'Nesbitt'. Vine vigor in 'Ga. 5-1-45' appears to be similar to the comparison cultivars of Table 6 below, indicating the vine should grow well enough to consistently set good yields. The only other recommended self-fertile purple cultivar is 'Nesbitt', which ripens mid to late season (see Table 1 below).

Plant Characteristics

Vines: The vines of 'Ga 5-1-45' grow vigorously i.e. the growth of lateral canes on mature vines in Tifton, Ga., has been observed to be about 110 cm per growing season, comparable to the growth rate of 'Supreme' and 'Nesbitt'. The trunk caliper measurement at 75 cm above the soil line averaged 24.7 mm for a typical three-year old vine.

Canes: Lateral canes are semi-drooping and usually grow 1 m or more in a season in Georgia. The color of mature canes is greyish brown (RHS 201A) and the bark is smooth. Typical cane diameter is about 3 to 12 mm. Internode length ranges from about 3 to 6 cm. Tendrils, averaging about 10 cm in length, are unbranched and discontinuous along the nodes.

Foliage: Typical leaves average 10 cm in length and 8.5 cm in width. The leaves are circular with broadly toothed margins and glabrous on both upper and lower surfaces. Mature upper leaf surfaces are dark green (RHS 137A) and somewhat dull, while the lower leaf surfaces are light green (RHS 137C) and shiny. Petiole length equals or slightly exceeds the blade middrib length and the petiole sinus is wide open.

Flowers: The flowers are self-fertile. The petals are yellow green (RHS 145B) and small (with the inflorescence less than about 1 cm in diameter), which is typical for the species. The functional cream-colored anthers (RHS 158A) are supported on long (4 mm) filaments at the base of the ovary. The flowers are short lived, lasting approximately 2 to 3 days. 'Ga 5-1-45' typically blooms from May $10^{th}$ to June $1^{st}$ at Tifton, Ga.

Fruit: The vines produce large, black colored fruit (RHS 202A) which ripen in a two-week period beginning around the first week in August in Tifton, Ga. [in 2010, the harvest dates were from Aug. 2, 2010 to Aug. 16, 2010 (see Table 1 below)]. At maturity, the berries weigh approximately 11 g each and average about 18% soluble solids (see Table 2 below). The berries are round and average about 26 mm (see Table 2 below) in diameter (Table 2, Tifton, Ga., 2008-2010), containing an average of 4 seeds per berry. The seeds were grey brown in color (RHS 199A). The berries have inconspicuous lenticels (too small to get a color reading). The berries separate from the pedicel with a relatively dry stem scar, i.e. less than 25% of the berries are torn at the point of detachment from the pedicel (see Table 2 below). The black color of the 'Ga 5-1-45' fruit is distinct from the bronze fruit of 'Triumph', and the greenish-bronze fruit of 'Fry'.

Comparisons with other Muscadine Grape Cultivars

The Tables 1-6 below compare 'Ga. 5-1-45' with some other known muscadine grape cultivars. 'Tara', 'Nesbitt', 'Fry' and 'Triumph' are all unpatented. 'Supreme' is the subject of U.S. Plant Pat. No. 7,267.

TABLE 1

Characteristics and Yield of 'Ga. 5-1-45' Compared to third season Muscadine Grape Cultivars in Tifton, Ga.

| Cultivar | Harvest dates | Yield (kg)/vine[z] | % Total yield |
|---|---|---|---|
| 'Ga. 5-1-45' | Aug. 2, 2010 | 1.0 | 7 |
| | Aug. 5, 2010 | 7.2 | 50 |
| | Aug. 16, 2010 | 6.3 | 43 |
| | TOTAL | 14.5 | |
| 'Tara' | Aug. 5, 2010 | 0.51 | 3 |
| | Aug. 12, 2010 | 9.6 | 53 |
| | Aug. 25, 2010 | 7.8 | 44 |
| | TOTAL | 17.9 | |
| 'Nesbitt' | Sep. 7, 2010 | 10.1 | 87 |
| | Sep. 23, 2010 | 1.5 | 13 |
| | TOTAL | 11.6 | |
| Significance | | NS | |

[z]Mean separation of total yields not significant by Duncan's multiple range test, $P < 0.05$.

TABLE 2

Flower and fruit attributes of 'Ga. 5-1-45' and standard muscadine cultivars at Tifton, Ga. in years 2008-2010.

| Cultivar | Flower type | Berry color | Berry weight (g)[z] | Berry diameter (mm)[z] | % Soluble solids[z] | % Dry scar[y,z] |
|---|---|---|---|---|---|---|
| 'Ga. 5-1-45' | SF | Purple | 11.3 ± 0.7 b | 26.1 | 18.1 a | 77 |
| 'Supreme' | F | Purple | 14.2 ± 2.7 a | 29.3 | 14.4 bc | 70 |
| 'Nesbitt' | SF | Purple | 10.2 ± 1.0 b | 27.0 | 13.1 c | 62 |
| 'Fry' | F | Bronze | 12.4 ± 1.8 ab | 28.0 | 15.2 b | 65 |
| 'Tara' | SF | Bronze | 11.1 ± 1.2 b | 25.8 | 15.2 b | 83 |
| Significance | | | P = 0.002 | NS | P = 0.001 | NS |

[z]A 10 berry sample was taken from a 2 vine plot twice per season each year to calculate berry attributes. Mean separation within columns by Duncan's multiple range test, $P < 0.05$.
[y]Dry scars represent the lack of skin tears or openings around the pedicel scar after picking.

TABLE 3

Change in firmness (g/mm) of 'Ga. 5-1-45' and test cultivars at harvest and after cold storage (0-1° C., 90-95% R.H.). Berries were evaluated at harvest, packaged in ventilated clamshell containers and placed in cold storage for two weeks. Berries were then brought out of cold storage allowed to warm for 24 h at room temperature (21° C.) and evaluated 1 and 4 days post-removal.

| Cultivar | Firmness (g/mm)[z] Day 0 | Firmness (g/mm)[z] Day 15 | Firmness (g/mm)[z] Day 18 |
|---|---|---|---|
| 'Ga. 5-1-45' | 396 b | 275 a | 258 a |
| 'Supreme' | 446 a | 309 a | 267 a |
| 'Tara' | 303 c | 209 b | 186 b |
| 'Fry' | 291 c | | 164 b |
| Significance | P = 0.001 | P = 0.007 | P = 0.001 |

[z]Values are means with n = 4 for 'Ga. 5-1-45' and Supreme and n = 2 for Tara and Fry. Each replication consisted of 25 berries measured for firmness using a Bioworks FirmTech II. Mean separation within columns by Duncan's multiple range test, $P < 0.05$.

TABLE 4

Harvest date and % soluble solids of 'Ga. 5-1-45' and the standard early cultivars 'Tara' and 'Triumph' at Tifton, Ga. 2007-2009.

| Year | Cultivar | Sample Date | Brix[z] |
|---|---|---|---|
| 2007 | 'Ga. 5-1-45' | 10 August | 19.6 a |
| | 'Tara' | 10 August | 15.5 c |
| | 'Triumph' | 10 August | 16.9 b |
| 2008 | 'Ga. 5-1-45' | 8 August | 19.8 a |
| | 'Tara' | 12 August | 16.7 b |
| | 'Triumph' | 5 August | 16.7 b |
| 2009 | 'Ga. 5-1-45' | 11 August | 17.7 a |
| | 'Tara' | 11 August | 14.0 b |
| | 'Triumph' | 11 August | 15.6 c |

[z]Mean separation of 10 berry samples within columns by Duncan's multiple range test, $P < 0.05$.

TABLE 5

Berry weight and diameter and coefficients of variation (COV) of 'Ga. 5-1-45' and 'Supreme' in years 2008-2010.

| Cultivar | Year | Berry weight (g) | COV | Berry diameter (mm) | COV |
|---|---|---|---|---|---|
| 'Ga. 5-1-45' | 2008 | 10.9 | 14.5 | 25.7 | 4.8 |
| | 2009 | 12.4 | 12.7 | 26.6 | 6.6 |
| | 2010 | 10.8 | 11.6 | 25.8 | 5.4 |
| | Mean | 11.4 | 12.9 | 26.0 | 5.6 |
| 'Supreme' | 2008 | 15.4 | 20.6 | 29.3 | 13.8 |
| | 2009 | 14.5 | 13 | 30.1 | 11.6 |
| | 2010 | 12.4 | 21.9 | 27 | 7.1 |
| | Mean | 14.1 | 18.5 | 28.8 | 10.8 |

TABLE 6

Vine caliper of 'Ga. 5-1-45' and test cultivars during first 3 years of growth in trials inTifton, Ga. and Athens, Ga.

| | Vine caliper (mm)[z] | | |
|---|---|---|---|
| Cultivar | Year 1 | Year 2 | Year 3 |
| Tifton, Ga. | | | |
| 'Ga. 5-1-45' | 8.5 | 15.2 a[y] | 24.7 |
| 'Nesbitt' | 7.3 | 17.7 b | 25.0 |
| 'Supreme' | 8.5 | — | — |
| Significance (P) | NS | 0.007 | NS |
| Athens, Ga. | | | |
| 'Ga. 5-1-45' | 7.0 | 18.0 | |
| 'Nesbitt' | 7.2 | 18.0 | |
| 'Supreme' | 8.0 | 15.8 | |
| Significance (P) | NS | NS | |

[z]Internode thickness measured 75 cm from the ground.
[y]Mean separation within columns by Duncan's multiple range test, $P < 0.05$.

What is claimed is:

1. A new and distinct muscadine grape plant, substantially as herein illustrated and described, characterized by early ripening berries, typically beginning in the first week in August in Georgia; purple berries; self-fertile flowers; berries with flesh that adheres to the skin (non-slip skin); berries that are firm in texture and with a high soluble solids content; and berries that are large for a self-fertile cultivar.

* * * * *